United States Patent [19]
Kuenzy

[11] 3,975,402
[45] Aug. 17, 1976

[54] PREPARATION OF N-[(1-ETHYL-PYRROLIDINYL-2)-METHYL]-2-METHOXY-5-SULPHAMOYL-BENZAMIDE

[75] Inventor: Fred Kuenzy, Pully, Switzerland
[73] Assignee: Fratmann S.A., Switzerland
[22] Filed: June 12, 1974
[21] Appl. No.: 478,764

Related U.S. Application Data
[63] Continuation of Ser. No. 197,515, Nov. 10, 1971, abandoned.

[30] Foreign Application Priority Data
Aug. 20, 1971 Switzerland............... 12267

[52] U.S. Cl. .......................................... 260/326.82
[51] Int. Cl.$^2$....................................... C07D 207/12
[58] Field of Search .............................. 260/326.82

[56] References Cited
OTHER PUBLICATIONS
Merck, Chem. Abst. 64: 3486–3488 (1966), Abs. of Neth. Pat. 6,500,326.
Grimmel, et al. *J. Am. Chem. Soc.*, 68: 539–542 (1946).

*Primary Examiner*—Frederick E. Waddell
*Attorney, Agent, or Firm*—Robert E. Burns; Emmanuel J. Lobato; Bruce L. Adams

[57] ABSTRACT

N-[(1-ethyl-pyrrolidinyl-2)-methyl]-2-methoxy-5-sulphamoyl-benzamide is prepared by reacting 1-ethyl-2-aminomethyl-pyrrolidine with 2-methoxy-5-sulphamoyl-benzoic acid in the presence of phosphorous trichloride with pyridine as reaction medium.

2 Claims, No Drawings

PREPARATION OF N-[(1-ETHYL-PYRROLIDINYL-2)-METHYL]-2-METHOXY-5-SULPHAMOYL-BENZAMIDE

This is a continuation of application Ser. No. 197,515, filed Nov. 10, 1971, now abandoned.

This invention relates to the preparation of N - [(1-ethyl-pyrrolidinyl-2)-methyl] -2-methoxy-5-sulphamoyl-benzamide.

According to the invention, a process for preparing N - [(1-ethyl-pyrrolidinyl-2)-methyl] -2-methoxy-5-sulphamoyl-benzamide comprises reacting 1-ethyl-2-aminomethyl-pyrrolidine and 2-methoxy-5-sulphamoyl-benzoic acid in the presence of phosphorous trichloride.

As reaction medium, pyridine can be used.

The reaction takes place according to the following schematic sequence:

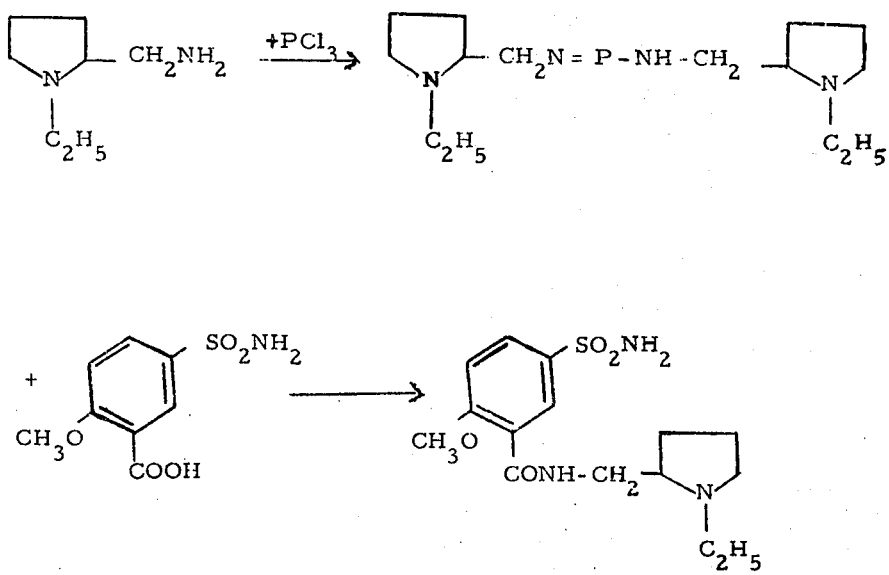

EXAMPLE

In a one liter flask with a stirrer, a condensor, a thermometer and a dropping funnel, 27 g (0.11 Mol) of 1-ethyl-2-aminomethyl-pyrrolidine and 560 ml of pyridine are introduced. The solution obtained is stirred and 5.6 g (0.04 Mol) of phosphorous trichloride dissolved in 64 ml pyridine are added drop-by-drop whilst maintaining the temperature at about 20°C.

After stirring at 20°C for an half-hour 14.8 g (0.064 Mol) of 2-methoxy-5-sulphamoyl-benzoic acid are added. The mixture is reflux heated during four and a half hours and allowed to rest overnight. The pyridine is then removed by distillation under vacuum and the residue extracted with 200 ml of 10 % hydrochloric acid. There is obtained a precipitate which is heated to about 70°–80°C and dissolved. This solution is treated with 15 ml of concentrated ammonia water. The precipitate formed is filtered, washed with water, and dried in a drying chamber at 50°C.

16.2 g (Yield 74.3 %) of N - [(1-ethyl-pyrrolidinyl-2)-methyl] -2-methoxy-5-sulphamoyl-benzamide with a melting point of 178°C are obtained.

N - [(1-ethyl-pyrrolidinyl-2)-methyl] -2-methoxy-5-sulphamoyl-benzamide is useful in the pharmaceutical industry as an intermediary product, in particular for the manufacture of pharmaceutical products for the treatment of sickness in the fields of gastroenterology and neurology.

I claim:

1. Process for preparing N-(1-ethyl-pyrrolidinyl-2)-methyl)-2-methoxy-5-sulphamoyl-benzamide which comprises the steps of reacting an excess of about two mol-equivalents of 1-ethyl-2-aminomethyl-pyrrolidine with one mol-equivalent of phosphorous trichloride in pyridine as the reaction medium and then reacting the resultant product with 2-methoxy-5-sulphamoyl-benzoic acid.

2. The process according to claim 1 wherein 11 mol-equivalents of 1-ethyl-2-aminomethyl pyrrolidine is reacted with about 4 mol-equivalents of phosphorous trichloride.

* * * * *